US012588825B2

(12) United States Patent
Young et al.

(10) Patent No.: US 12,588,825 B2
(45) Date of Patent: Mar. 31, 2026

(54) INFLATABLE CUFFS WITH CONTROLLABLE EXTENSIBILITY

(71) Applicant: Apple Inc., Cupertino, CA (US)

(72) Inventors: Derek Park-Shing Young, Fremont, CA (US); Joseph M. Schmitt, Cupertino, CA (US); Zijing Zeng, San Jose, CA (US); Erno H. Klaassen, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 1228 days.

(21) Appl. No.: 17/279,841

(22) PCT Filed: Sep. 23, 2019

(86) PCT No.: PCT/US2019/052362
§ 371 (c)(1),
(2) Date: Mar. 25, 2021

(87) PCT Pub. No.: WO2020/068626
PCT Pub. Date: Apr. 2, 2020

(65) Prior Publication Data
US 2021/0393152 A1      Dec. 23, 2021

Related U.S. Application Data

(60) Provisional application No. 62/738,445, filed on Sep. 28, 2018.

(51) Int. Cl.
*A61B 5/00*            (2006.01)
*A61B 5/022*          (2006.01)
(Continued)

(52) U.S. Cl.
CPC ................... *A61B 5/02233* (2013.01); *A61B 2017/00199* (2013.01); *A61B 2017/00221* (2013.01); *A61B 2017/00398* (2013.01); *A61B 17/1355* (2013.01)

(58) Field of Classification Search
None
See application file for complete search history.

(56) References Cited

U.S. PATENT DOCUMENTS 3,752,148 A        8/1973    Schmalzbach
5,772,034 A  *    6/1998    Lin ...................... B65D 31/147
                                                        206/524.8
(Continued)

OTHER PUBLICATIONS

Karagozler et al., "Electrostatic Latching for Inter-Module Adhesion, Power Transfer, and Communication in Modular Robots", In Proceedings of the IEEE International Conference on Intelligent Robots and Systems (IROS '07), Oct. 2007, pp. 1-8.
(Continued)

*Primary Examiner* — Charles A Marmor, II
*Assistant Examiner* — Destiny J Cruickshank
(74) *Attorney, Agent, or Firm* — Kilpatrick Townsend & Stockton LLP

(57) ABSTRACT

A blood pressure cuff includes a support band that is selectively reconfigured between a flexible standby configuration and a measurement configuration. A blood pressure cuff includes an inflatable bladder, a support band, and a control unit. The support band is attached to and surrounds the inflatable bladder. The support band is reconfigurable, in response to an input from the control unit, from a standby configuration for between blood pressure measurements to a measurement configuration for constraining the inflatable bladder while the inflatable bladder is in an inflated state during a blood pressure measurement. The control unit includes a bladder pump for inflation of the inflatable bladder during a blood pressure measurement and controls the selective reconfiguration of the support band.

17 Claims, 11 Drawing Sheets

(51) Int. Cl.
    *A61B 17/00*         (2006.01)
    *A61B 17/135*        (2006.01)

(56)                    References Cited

U.S. PATENT DOCUMENTS

| | | | |
|---|---|---|---|
| 6,336,901 B1 | 1/2002 | Itonaga et al. | |
| 2002/0170359 A1 | 11/2002 | Yamakoshi et al. | |
| 2010/0106029 A1* | 4/2010 | Fraden ............... | A61B 5/02208 |
| | | | 600/490 |
| 2012/0249766 A1* | 10/2012 | Narusawa .......... | A61B 5/02438 |
| | | | 348/E7.085 |
| 2013/0261405 A1* | 10/2013 | Lee ........................ | A61B 5/318 |
| | | | 600/509 |
| 2015/0183535 A1* | 7/2015 | Vardakostas ............ | B65B 43/14 |
| | | | 53/72 |
| 2015/0305974 A1* | 10/2015 | Ehrenreich .......... | A61B 5/6833 |
| | | | 601/46 |

OTHER PUBLICATIONS

Pelrine et al., "Electrostriction of Polymer Dielectrics with Compliant Electrodes as a means of Actuation", Sensors and Actuators, vol. 64, Issue 1, Jan. 1, 1998, pp. 77-85.

* cited by examiner

FIG. 2
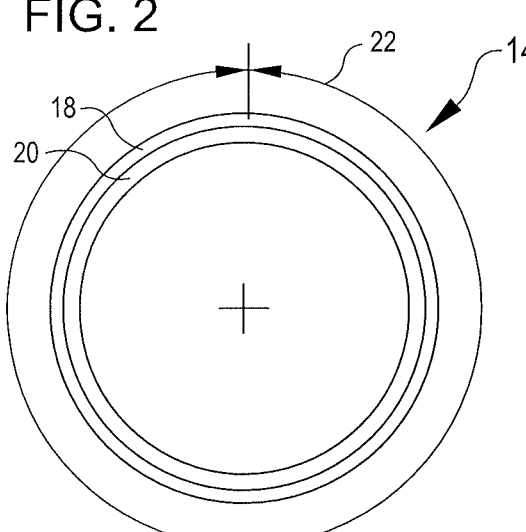
FIG. 3
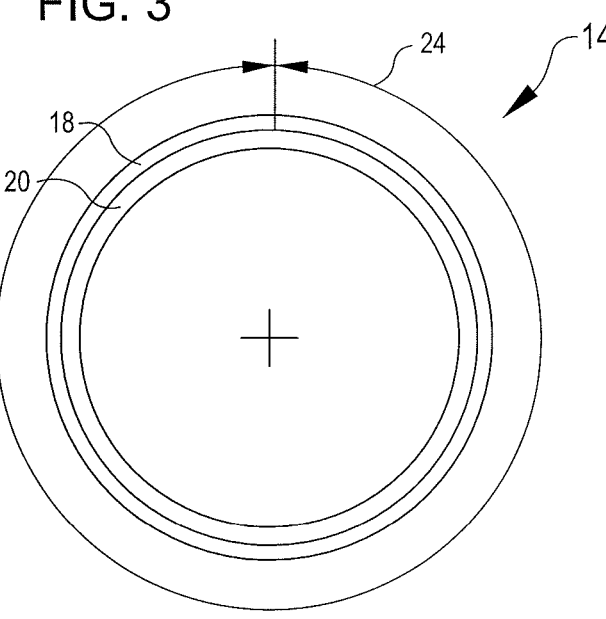
FIG. 4
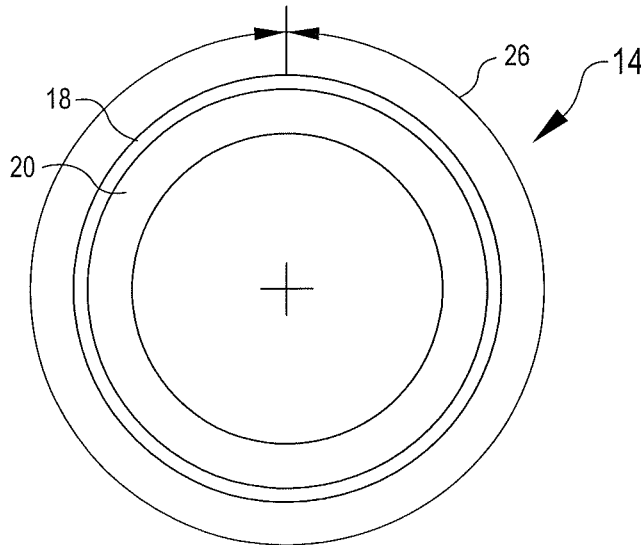

FIG. 9
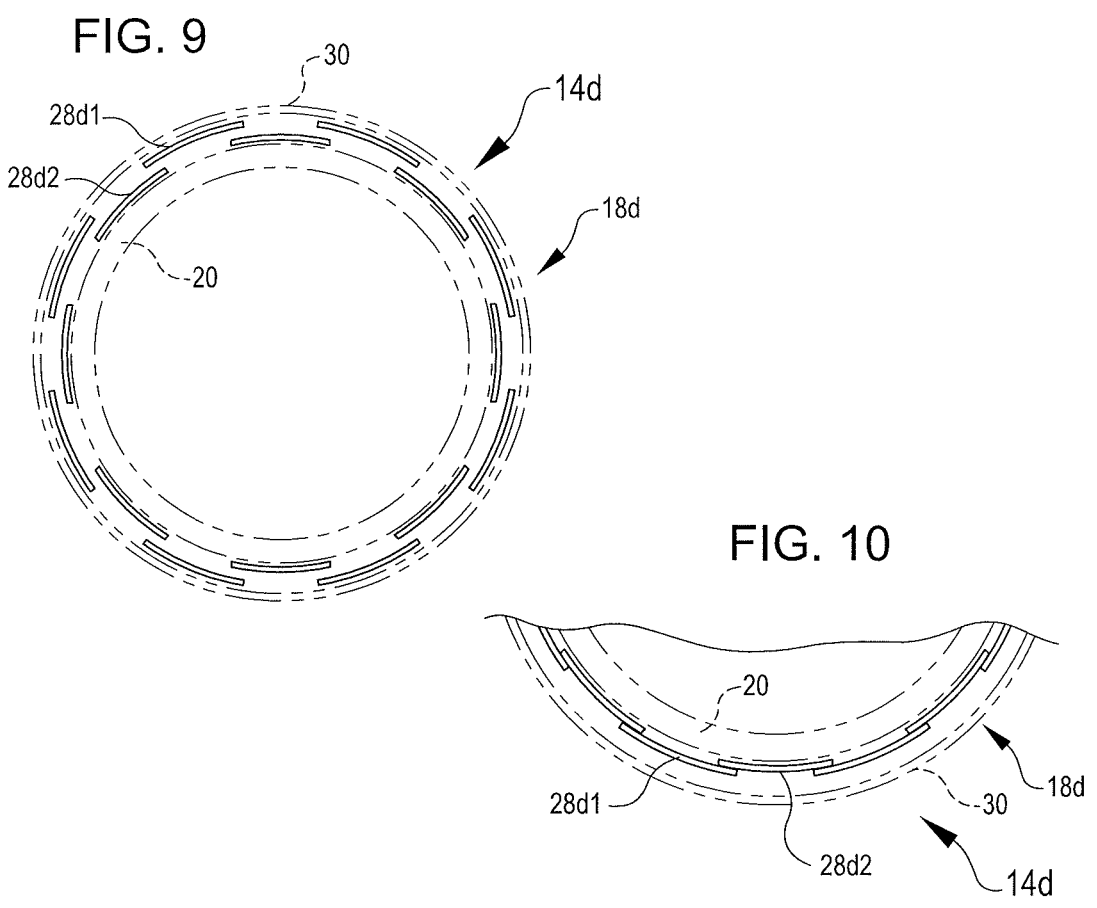
FIG. 10
FIG. 11
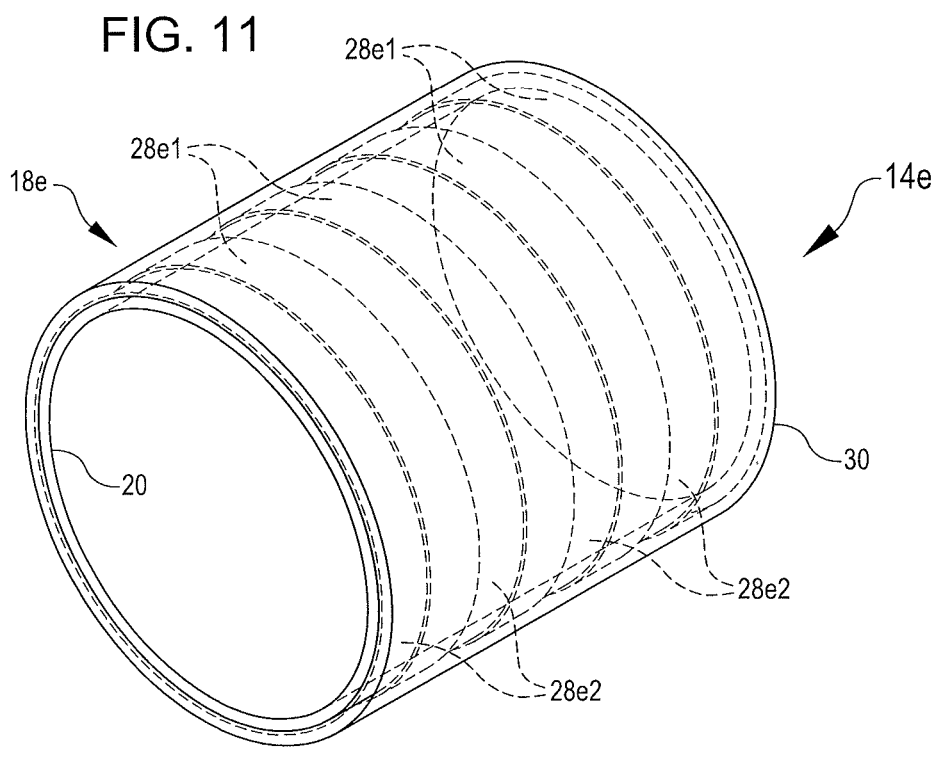

Vent Hole
54

56
Hinge

52
Vent cover
(electrostatically sealed)

INFLATABLE CUFFS WITH CONTROLLABLE EXTENSIBILITY

The present application is a U.S. National Stage Application of PCT/US2019/052362 filed Sep. 23, 2019; which claims the benefit under 35 USC § 119(e) of U.S. Provisional Appln. No. 62/738,445 filed Sep. 28, 2018; the full disclosures which are incorporated herein by reference in their entirety for all purposes.

BACKGROUND

Elevated blood pressure (a.k.a. hypertension) is a major risk factor for cardiovascular disease. As a result, blood pressure measurement is a routine task in many medical examinations. Timely detection of hypertension can help inhibit related cardiovascular damage via accomplishment of effective efforts in treating and/or controlling hypertension.

Blood pressure is a continuously changing vital parameter. As a result, sporadic office blood pressure measurements may be insufficient to detect some forms of hypertension. For example, hypertension can occur in a pattern that evades detection via isolated office blood pressure measurement. Common hypertension patterns include white coat hypertension (elevated only during a limited period of time), borderline hypertension (fluctuating above and below definitional levels over time), nocturnal hypertension (elevated only during sleeping hours or not showing the normal drop in pressure during sleep), isolated systolic hypertension (elevated systolic pressure with non-elevated diastolic pressure), and isolated diastolic hypertension (elevated diastolic pressure with non-elevated systolic pressure). To detect such hypertension patterns, it may be necessary to perform additional blood pressure measurements over time to obtain a more complete view of a person's blood pressure characteristics. Although continuous measurement of blood pressure can be achieved by invasive means, for example, via an intra-arterial pressure sensing catheter, noninvasive blood pressure measurement approaches are more typically used.

Current noninvasive blood pressure measurement approaches include ambulatory and home blood pressure measurement strategies. These strategies provide such a more complete view of a person's blood pressure characteristics and are often employed in recommended situations. Ambulatory blood pressure measurement is performed while the person performs daily life activities. Currently, ambulatory blood pressure measurements are typically performed every 20 to 30 minutes. Ambulatory blood pressure measurement may be recommended where there is large variability in office blood pressure measurements, where a high office blood pressure is measured in a person with otherwise low cardiovascular risk, when office and home blood pressure measurements vary, where resistance to drug treatment of blood pressure is noted or suspected, where hypotensive episodes are suspected, or where pre-eclampsia is suspected in pregnant women. Home blood pressure measurements include isolated self-measurements performed by a person at home. Home blood pressure measurements may be recommended where information is desired regarding the effectiveness of blood pressure lowering medication over one or more dose-to-dose intervals and/or where doubt exists as to the reliability of ambulatory blood pressure measurement.

BRIEF SUMMARY

Ambulatory blood pressure measurements cuffs, and related methods, employ a support band that is reconfigured via a control unit between a flexible standby configuration for between blood pressure measurements and a measurement configuration for constraining an inflatable bladder during a blood pressure measurement. In some embodiments, the support band includes one or more reinforcement sheets embedded within a flexible band. One or more electrodes are formed on the one or more reinforcement sheets. In the flexible standby configuration, the electrodes are not energized and the one or reinforcement sheets are free to move so as to accommodate changes in circumference of the flexible band to limit the pressure applied by the blood pressure cuff to a user's limb to a comfortable level during movement and/or flexing of the user's limb. In the measurement configuration, the electrodes are energized so as to electrostatically bind the electrodes together, thereby constraining the reinforcement sheets to inhibit changes in the circumference of the flexible band to provide suitable support to the inflatable bladder during an inflation of the inflatable bladder during a blood pressure measurement. Following completion of the blood pressure measurement, the electrodes are de-energized, thereby returning the support band back to the flexible standby configuration. In some embodiments, an inflatable support band is employed that is inflated to reconfigure the inflatable support band from a flexible standby configuration for between blood pressure measurements and a measurement configuration for constraining an inflatable bladder during a blood pressure measurement. Accordingly, an ambulatory blood pressure measurement cuff as described herein can provide increased user comfort between blood pressure measurements and be automatically reconfigured, via a control unit, to a measurement configuration for use during a blood pressure measurement, and then automatically reconfigured back to the flexible standby configuration following the blood pressure measurement. The ambulatory blood pressure measurement cuffs, devices, and approaches described herein can be configured for use on any suitable limb of a user including, but not limited to, a user's wrist, a user's thigh, a user's leg, a user's arm, and a user's upper arm.

Thus, in one aspect, a blood pressure cuff includes an inflatable bladder, a support band attached to and surrounding the inflatable bladder, and a control unit. The support band is reconfigurable, in response to an input, from a standby configuration for between blood pressure measurements to a measurement configuration for constraining the inflatable bladder while the inflatable bladder is in an inflated state during a blood pressure measurement. A circumferential stiffness of the support band is at least 50 percent greater in the measurement configuration than in the standby configuration. The control unit includes a bladder pump for inflation of the inflatable bladder during a blood pressure measurement and a support band control unit for supplying the input to the support band. In some embodiments, the circumferential stiffness of the support band is at least 100 percent greater in the measurement configuration than in the standby configuration. In some embodiments, the circumferential stiffness of the support band is at least 200 percent greater in the measurement configuration than in the standby configuration.

In many embodiments, the support band reconfigures from the standby configuration to the measurement configuration in response to a voltage input. For example, in one configuration, the support band includes a sheet of a material extending circumferentially around the support band over greater than 360 degrees; a first surface electrode is formed on a first end portion of the sheet; a second surface electrode is formed on a second end portion of the sheet separated from the first end portion by an intervening portion of the sheet; the first surface electrode and the second surface electrode overlap; the first surface electrode and the second surface electrode are operatively connected to the support band control unit for activation via the input; separation between the first surface electrode and the second surface electrode accommodates slippage between the first surface electrode and the second surface electrode when the first surface electrode and the second surface electrode are not activated via the input; and activation of the first surface electrode and the second surface electrode via the input electrostatically binds the first surface electrode and the second surface electrode so as to prevent slippage between the first surface electrode and the second surface electrode. In some embodiments, at least one of the first end portion and the second end portion includes at least two isolated circumferentially extending portions. In some embodiments, the sheet is embedded within a stretchable fabric band.

In another configuration, the support band includes a first sheet of a material extending circumferentially around the support band and a second sheet of a material extending circumferentially around the support band; a first surface electrode is formed on the first sheet; a second surface electrode is formed on the second sheet; the first surface electrode and the second surface electrode overlap; the first surface electrode and the second surface electrode are operatively connected to the support band control unit for activation via the input; separation between the first surface electrode and the second surface electrode accommodates slippage between the first surface electrode and the second surface electrode when the first surface electrode and the second surface electrode are not activated via the input; and activation of the first surface electrode and the second surface electrode via the input electrostatically binds the first surface electrode and the second surface electrode so that the first sheet and the second sheet are connected to form a continuous reinforcement ring in the measurement configuration. In some embodiments, the first sheet and the second sheet are embedded within a stretchable fabric band.

In another configuration, the support band includes a first plurality of longitudinally extending sheet segments and a second plurality of longitudinally extending sheet elements; first surface electrodes are formed on the first plurality of longitudinally extending sheet segments; second surface electrodes are formed on the second plurality of longitudinally extending sheet segments; each of the first surface electrodes overlaps each of an adjacent pair of the second surface electrodes; the first surface electrodes and the second surface electrodes are operatively connected to the support band control unit for activation via the input; separation between the first surface electrodes and the second surface electrodes accommodates slippage between the first surface electrodes and the second surface electrodes when the first surface electrodes and the second surface electrodes are not activated via the input; and activation of the first surface electrodes and the second surface electrodes via the input electrostatically binds the first plurality of longitudinally extending sheet segments and the second plurality of longitudinally extending sheet elements to form a continuous reinforcement ring in the measurement configuration. In some embodiments, the first plurality of longitudinally extending sheet segments and the second plurality of longitudinally extending sheet elements are embedded within a stretchable fabric band.

In another configuration, the support band includes a first plurality of circumferentially extending sheet segments and a second plurality of circumferentially extending sheet elements; first surface electrodes are formed on the first plurality of circumferentially extending sheet segments; second surface electrodes are formed on the second plurality of circumferentially extending sheet segments; each of the first surface electrodes overlaps at least one of the second surface electrodes; the first surface electrodes and the second surface electrodes are operatively connected to the support band control unit for activation via the input; separation between the first surface electrodes and the second surface electrodes accommodates slippage between the first surface electrodes and the second surface electrodes when the first surface electrodes and the second surface electrodes are not activated via the input; and activation of the first surface electrodes and the second surface electrodes via the input electrostatically binds the first plurality of circumferentially extending sheet segments and the second plurality of circumferentially extending sheet elements to form one or more continuous reinforcement rings in the measurement configuration. In some embodiments, the first plurality of circumferentially extending sheet segments and the second plurality of circumferentially extending sheet elements are embedded within a stretchable fabric band.

In another configuration, the support band includes a first plurality of sheet segments arranged in a first two-dimensional pattern and a second plurality of sheet elements arranged in a second two-dimensional pattern; first surface electrodes are formed on the first plurality of sheet segments; second surface electrodes are formed on the second plurality of sheet segments; each of the first surface electrodes overlaps at least two of the second surface electrodes; the first surface electrodes and the second surface electrodes are operatively connected to the support band control unit for activation via the input; separation between the first surface electrodes and the second surface electrodes accommodates slippage between the first surface electrodes and the second surface electrodes when the first surface electrodes and the second surface electrodes are not activated via the input; and activation of the first surface electrodes and the second surface electrodes via the input electrostatically binds the first plurality of sheet segments and the second plurality of sheet elements to form one or more continuous reinforcement rings in the measurement configuration. In some embodiments, the first plurality of sheet segments and the second plurality of sheet elements are embedded within a stretchable fabric band.

In some embodiments, the bladder includes an electrostatically sealable vent operable to vent air from the bladder. The electrostatically sealable vent can include a vent cover coupled with the bladder and configured to seal a vent hole in the bladder, a vent cover electrode being formed on the vent cover, a vent hole electrode formed on the bladder and surrounding the vent hole, the vent cover electrode and the vent hole electrode being operatively connected to the control unit. In some embodiments, the electrostatically sealable vent includes a tether and/or a spring mechanism connected to the vent cover and configured to limit an open orientation of the vent cover.

In some embodiments, the bladder includes an expansion chamber that is inflatable to increase a longitudinal length of the bladder. The bladder can include a plurality of electrostatically sealable vents operatively connected to the support band control unit and operable to inflate and deflate the expansion chamber.

In another aspect, a blood pressure cuff includes an inflatable bladder, an inflatable support band attached to and surrounding the inflatable bladder, and a control unit. The inflatable support band has an uninflated configuration for between blood pressure measurements and an inflated configuration for constraining the inflatable bladder while the inflatable bladder is in an inflated state during a blood pressure measurement. The control unit includes at least one pump for inflating the inflatable support band and the inflatable bladder for a blood pressure measurement.

In many embodiments, the inflatable support band is configured to be flexible in the uninflated configuration over a range of limb circumferences. For example, the inflatable support band can include an outer wall, an inner wall, and side walls that connect the outer wall to the inner wall; the inner wall can have an inner wall circumferential in-plane stiffness; and the outer wall can have an outer wall circumferential in-plane stiffness that is at least 100 percent greater than the inner wall circumferential in-plane stiffness.

In another aspect, a method of measuring a blood pressure of a person includes: (a) supporting an inflatable bladder in an uninflated state via a support band attached to and surrounding the inflatable bladder so as to maintain contact between the inflatable bladder in the uninflated state and a limb of the person; (b) supplying, via a control unit operatively coupled with the support band, an input to the support band that reconfigures the support band from a standby configuration having a standby configuration circumferential stiffness to a measurement configuration having a measurement configuration circumferential stiffness that is at least 50 percent greater than the standby configuration circumferential stiffness; and (c) with the support band in the measurement configuration, measuring, by the control unit, a blood pressure of the patient via an inflation of the inflatable bladder. In many embodiments, the method further includes, subsequent to the measurement of the blood pressure, reconfiguring the support band, via the control unit, from the measurement configuration to the standby configuration. In many embodiments, supplying the input to the support band includes supplying a voltage to electrodes formed on one or more reinforcement sheets so as to electrostatically bind the electrodes.

In another aspect, a method of measuring a blood pressure of a person includes: (a) supporting an inflatable bladder in an uninflated state via an inflatable support band attached to and surrounding the inflatable bladder so as to maintain contact between the inflatable bladder in the uninflated state and a limb of the person; (b) inflating the inflatable support band, via a control unit operatively coupled with the inflatable support band; and (c) with the support band inflated, measuring, by the control unit, a blood pressure of the patient via an inflation of the inflatable bladder. In many embodiments, the method further includes, subsequent to the measurement of the blood pressure, deflating the support band via the control unit.

The details of one or more implementations are set forth in the accompanying drawings and the description below. A better understanding of the features and advantages of the present invention will be obtained by reference to the description and drawings, and from the claims.

6

Figures 1A, 1B:
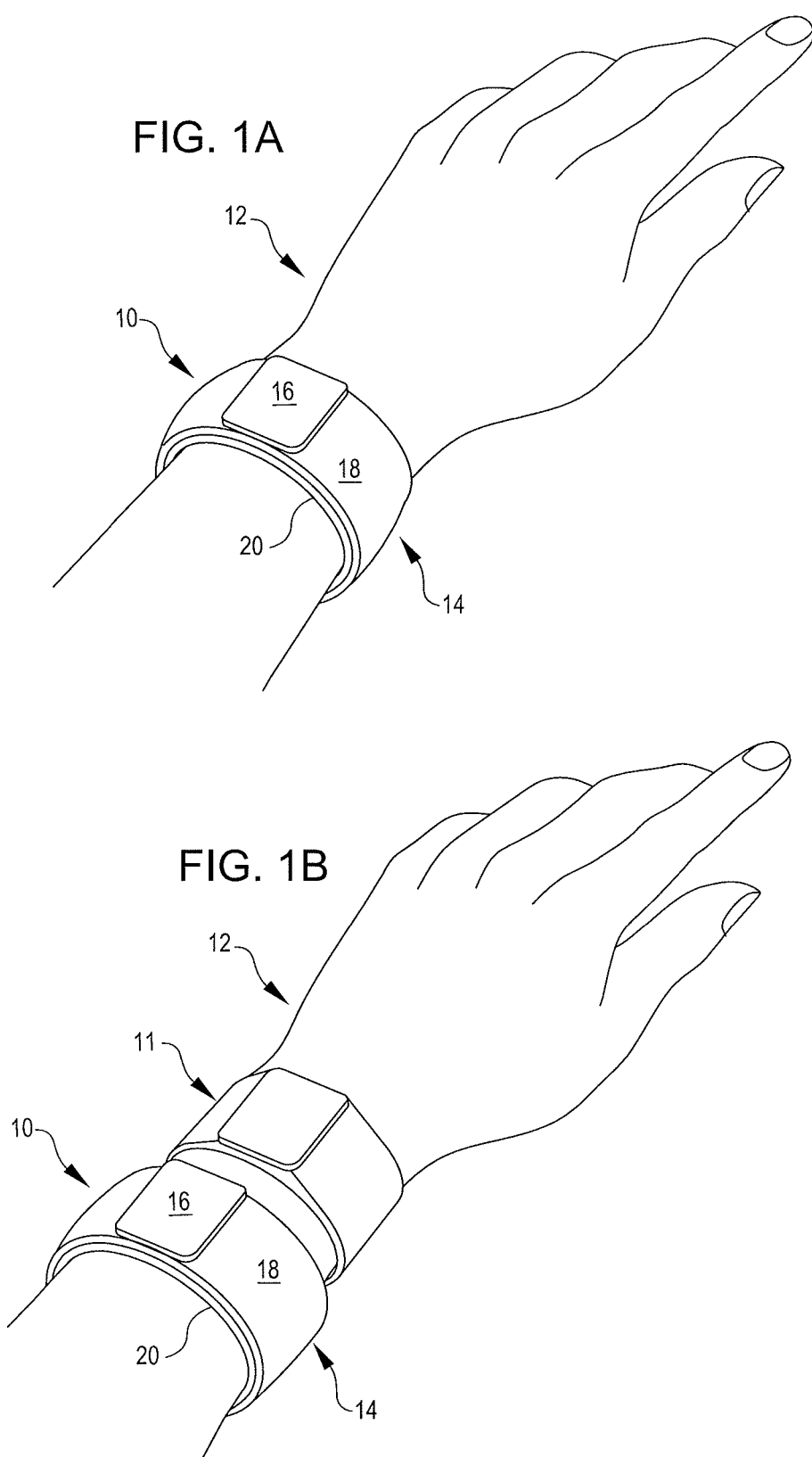
FIG. 1A shows an embodiment of an ambulatory blood pressure measurement device configured to be worn on a wrist of a user.
FIG. 1B shows another embodiment of the ambulatory blood pressure measurement device of FIG. 1A configured to be worn on a wrist of a user.
Figure 1C:
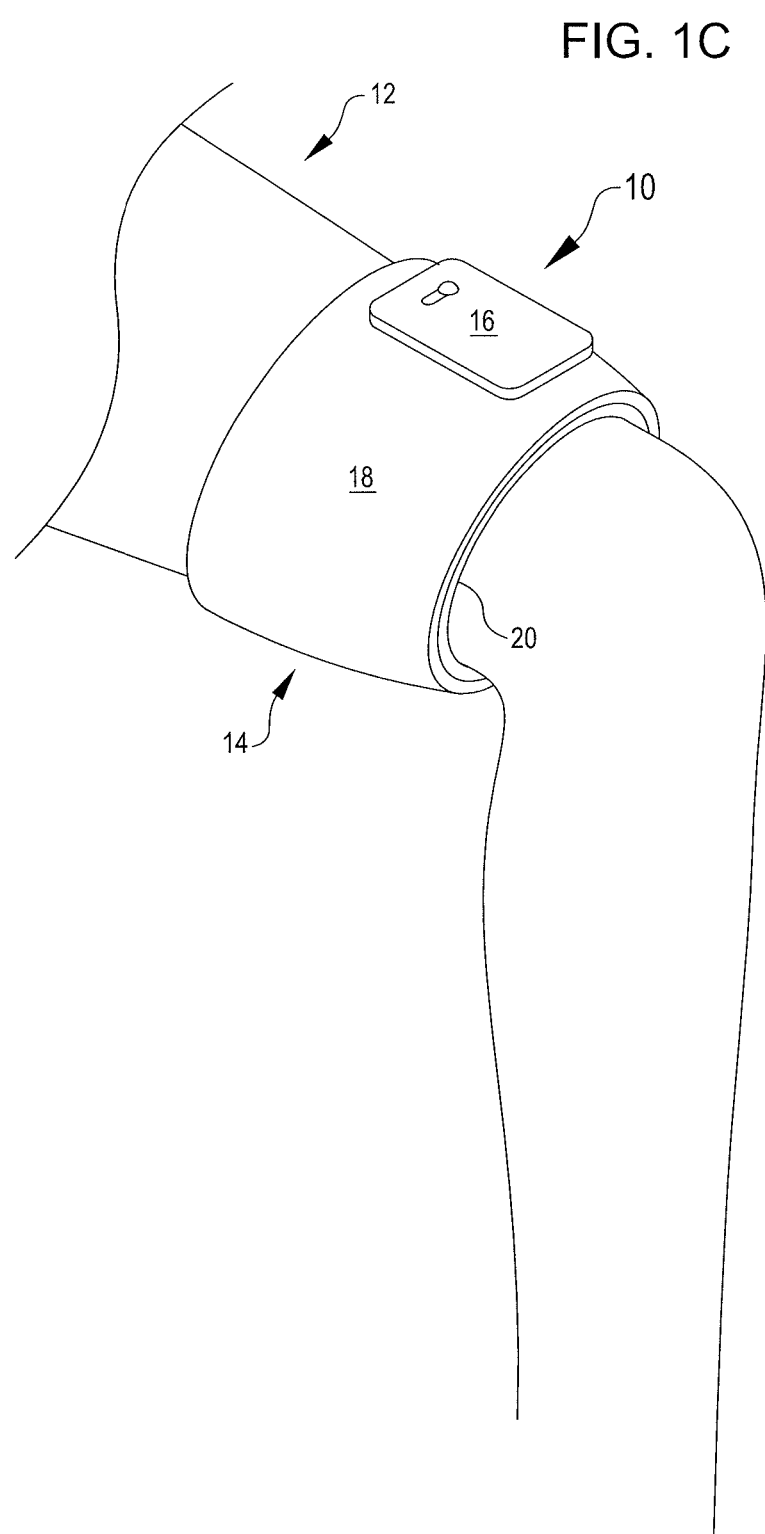

FIG. 1C shows an embodiment of the ambulatory blood pressure measurement device of FIG. 1A configured to be worn on a thigh of a user.

Figure 1D:
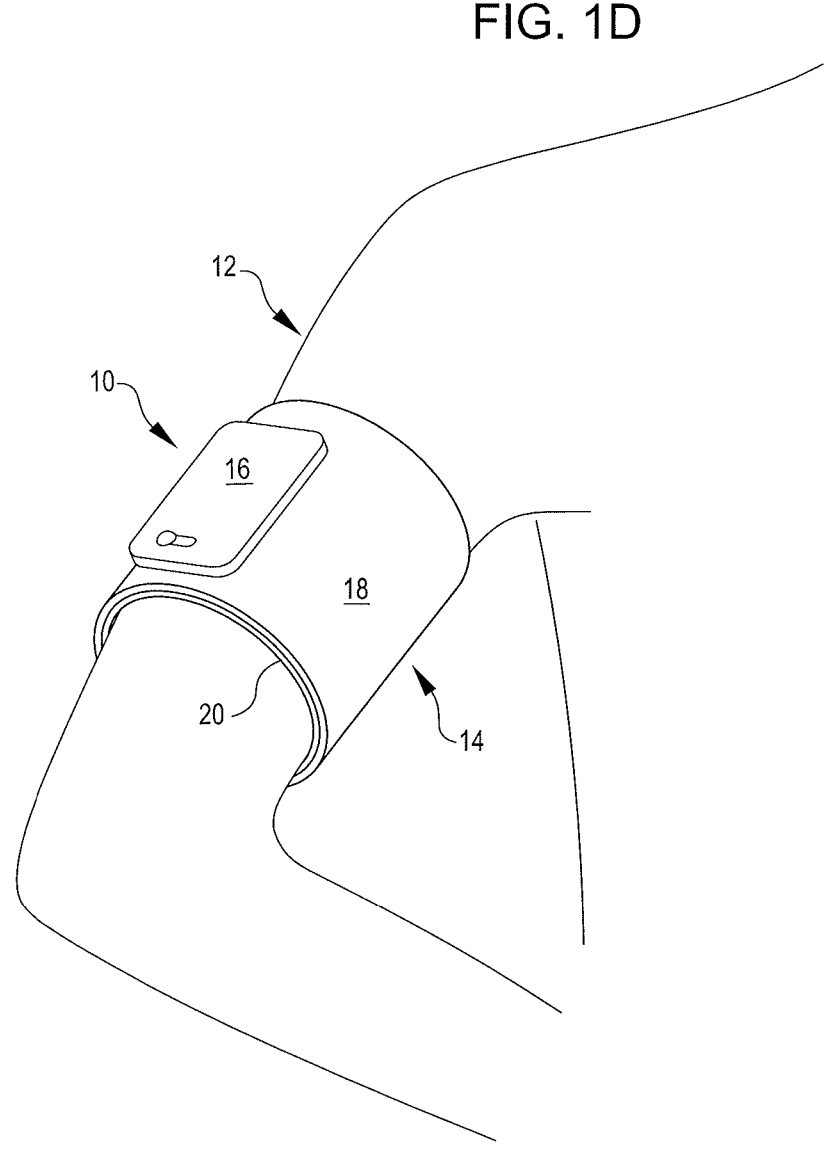

FIG. 1D shows an embodiment of the ambulatory blood pressure measurement device of FIG. 1A configured to be worn on an upper arm of a user.

FIG. 2 and FIG. 3 are cross-sectional views of an ambulatory blood pressure cuff illustrating changes in circumference in a flexible standby configuration of the blood pressure cuff.

FIG. 4 is a cross-sectional view of an ambulatory blood pressure cuff in a measurement configuration.

Figure 5:
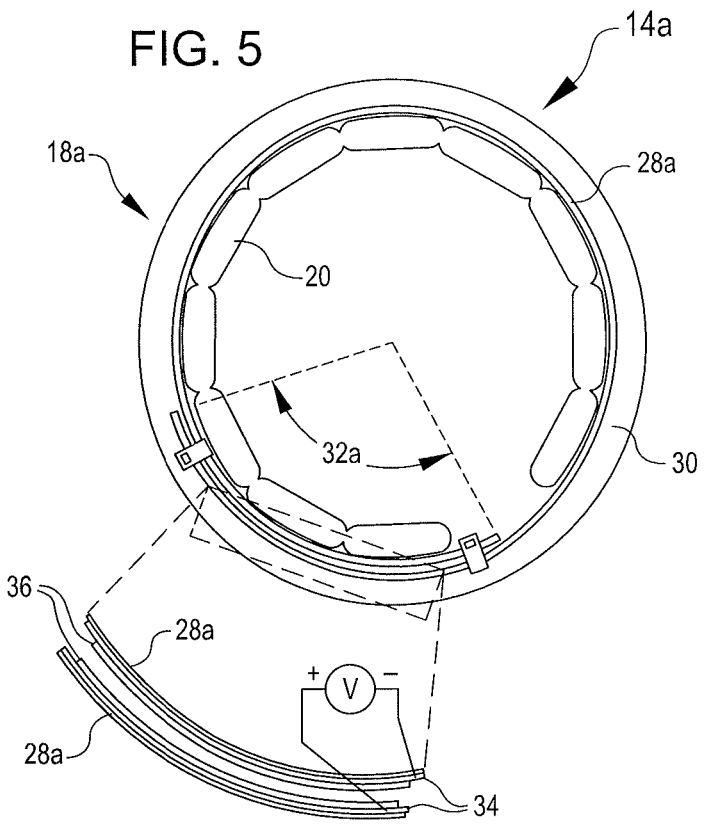

FIG. 5 is a cross-sectional view of an ambulatory blood pressure cuff that includes a reinforcement sheet with surface electrodes that are energized to reconfigure the reinforcement sheet into a continuous reinforcement band to reconfigure the blood pressure cuff from a flexible standby configuration to a measurement configuration, in accordance with embodiments.

Figure 6:
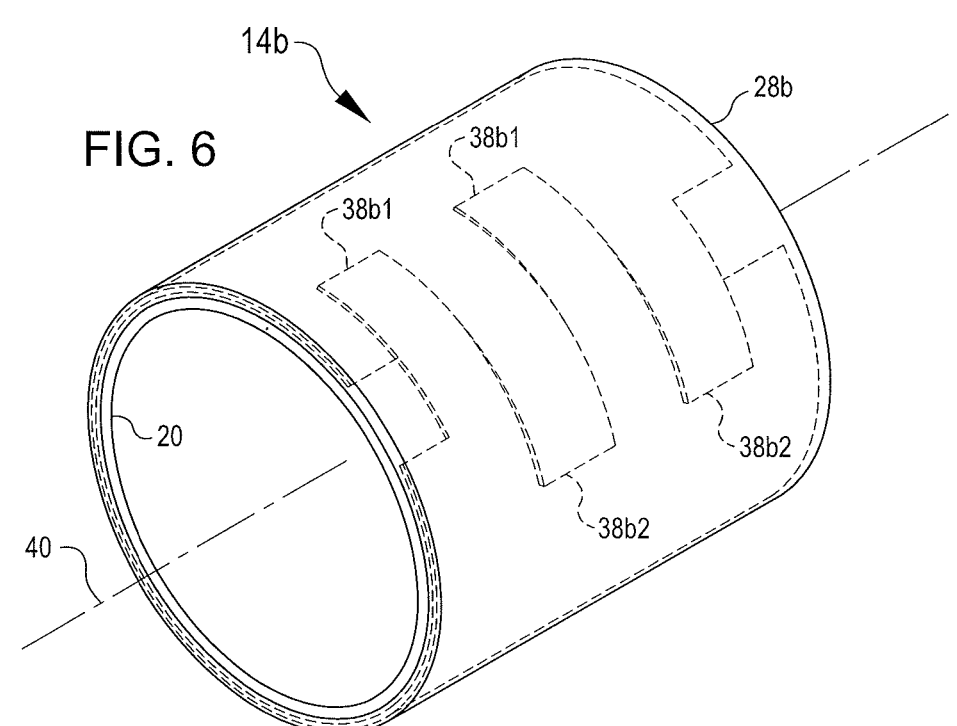

FIG. 6 shows an embodiment of the blood pressure cuff of FIG. 5 that includes isolated circumferentially extending end portions.

Figure 7:
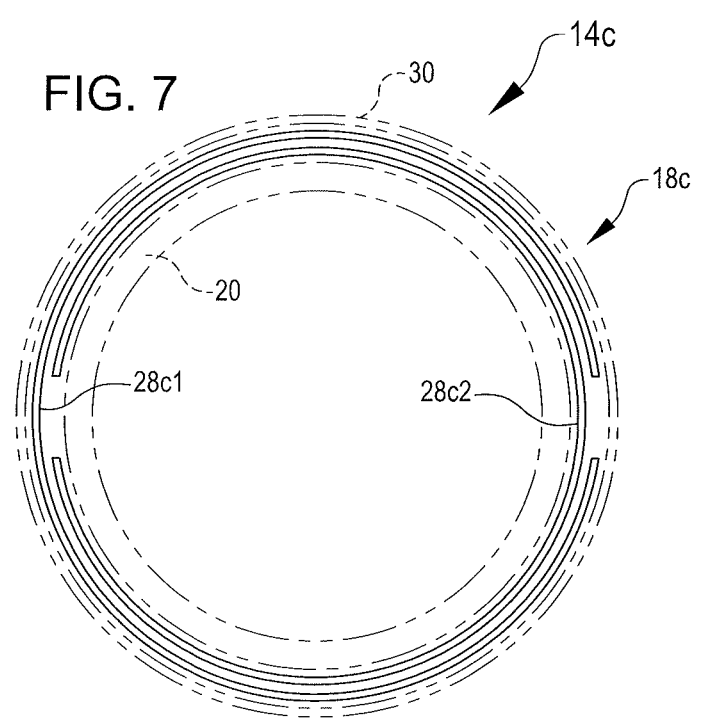

FIG. 7 is a cross-sectional view of an ambulatory blood pressure cuff that includes two overlapping reinforcement sheets with surface electrodes that are energized to bind the reinforcement sheets together to form a continuous reinforcement band to reconfigure the blood pressure cuff from a flexible standby configuration to a measurement configuration, in accordance with embodiments.

Figure 8:
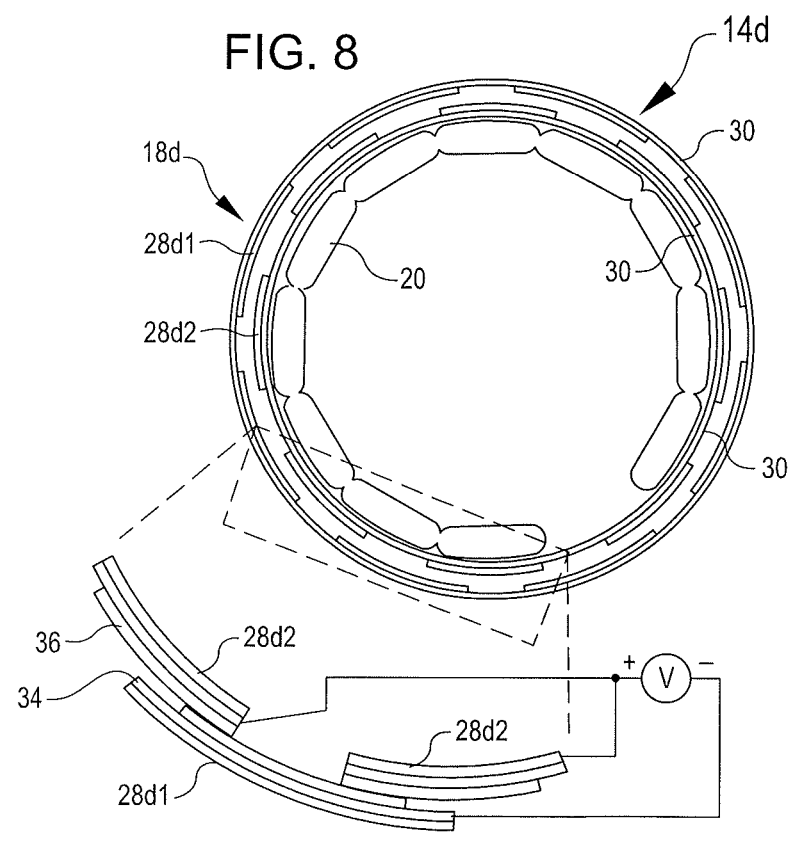

FIG. 8 through FIG. 10 are cross-sectional views of an ambulatory blood pressure cuff that includes longitudinally extending sheet reinforcement sheets segments with surface electrodes that are energized to bind the reinforcement sheets together to form a continuous reinforcement band to reconfigure the blood pressure cuff from a flexible standby configuration to a measurement configuration, in accordance with embodiments.

FIG. 11 shows an ambulatory blood pressure cuff that includes circumferentially extending reinforcement sheet segments with surface electrodes that are energized to bind the reinforcement sheet segments together to form one or more continuous reinforcement bands to reconfigure the blood pressure cuff from a flexible standby configuration to a measurement configuration, in accordance with embodiments.

Figure 12:
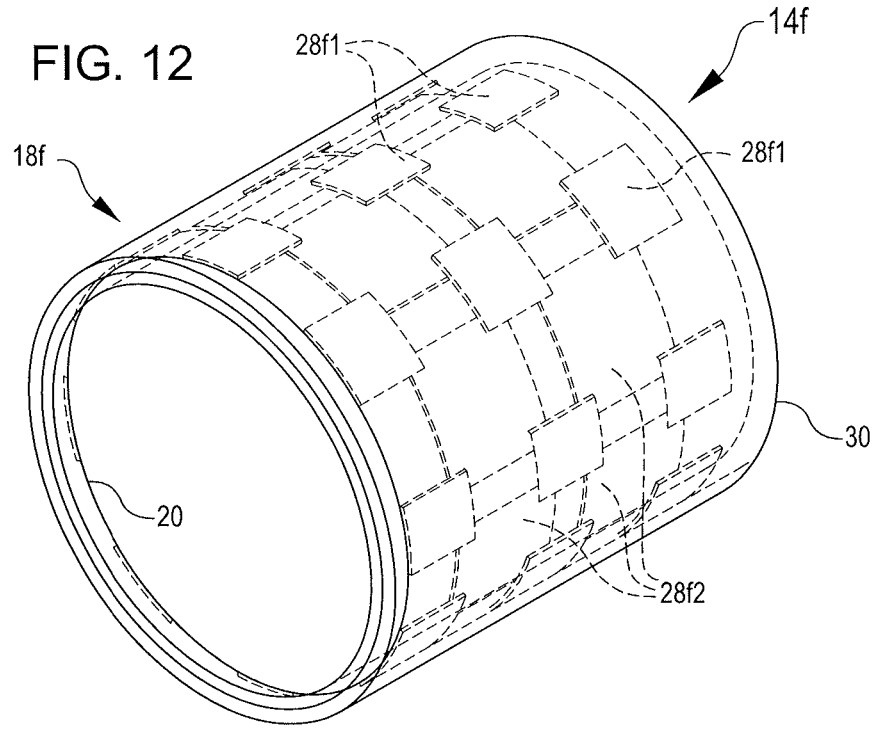

FIG. 12 shows an ambulatory blood pressure cuff that includes two-dimensional patterns of reinforcement sheet segments with surface electrodes that are energized to bind the reinforcement sheet segments together to form a continuous reinforcement band to reconfigure the blood pressure cuff from a flexible standby configuration to a measurement configuration, in accordance with embodiments.

Figure 13:
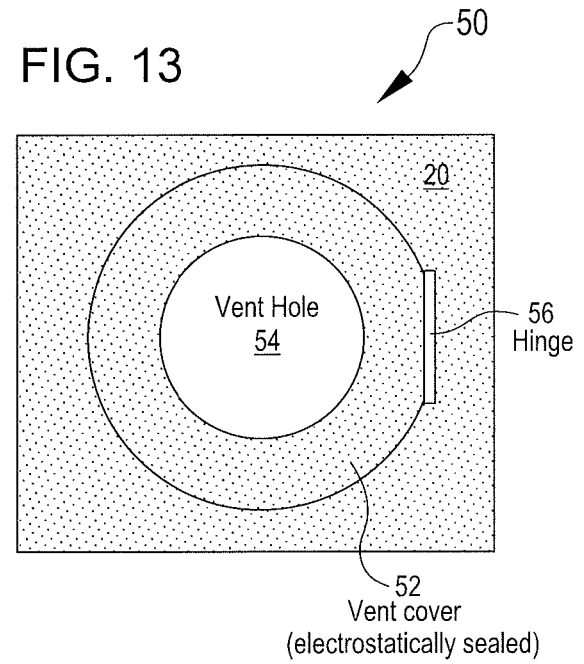

FIG. 13 illustrates an electrostatic vent assembly of an ambulatory blood pressure cuff, in accordance with embodiments.

Figure 14:
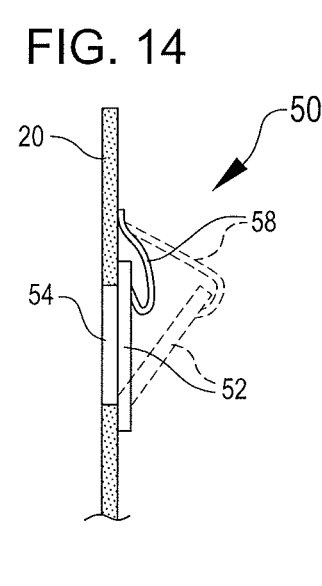

FIG. 14 is a side cross-sectional view of the electrostatic vent assembly of FIG. 13.

Figures 15, 16:
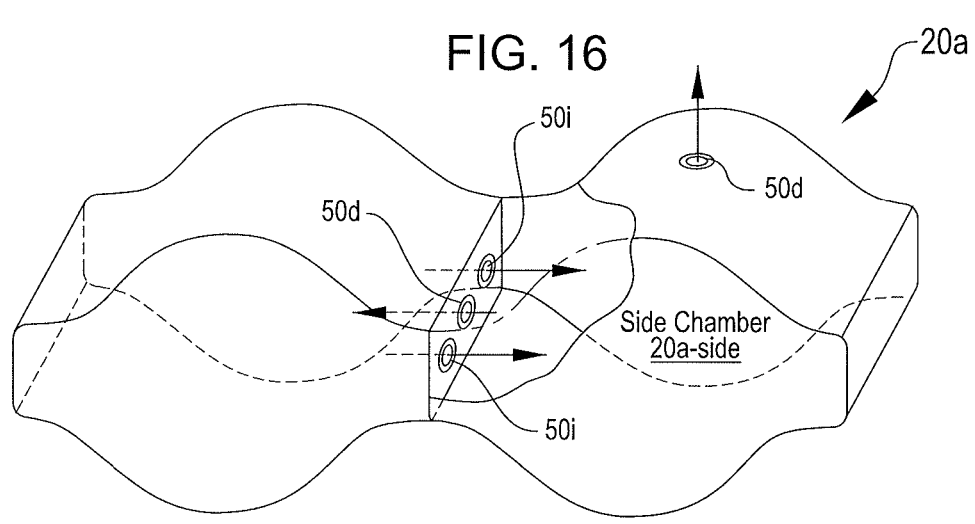

FIG. 15 shows an ambulatory blood pressure cuff that has an automatically configurable width, in accordance with embodiments.

FIG. 16 shows an inflatable side chamber and associated electrostatic inflation vents and electrostatic deflation vents for an embodiment of the blood pressure cuff of FIG. 15.

Figures 17, 18, 19:
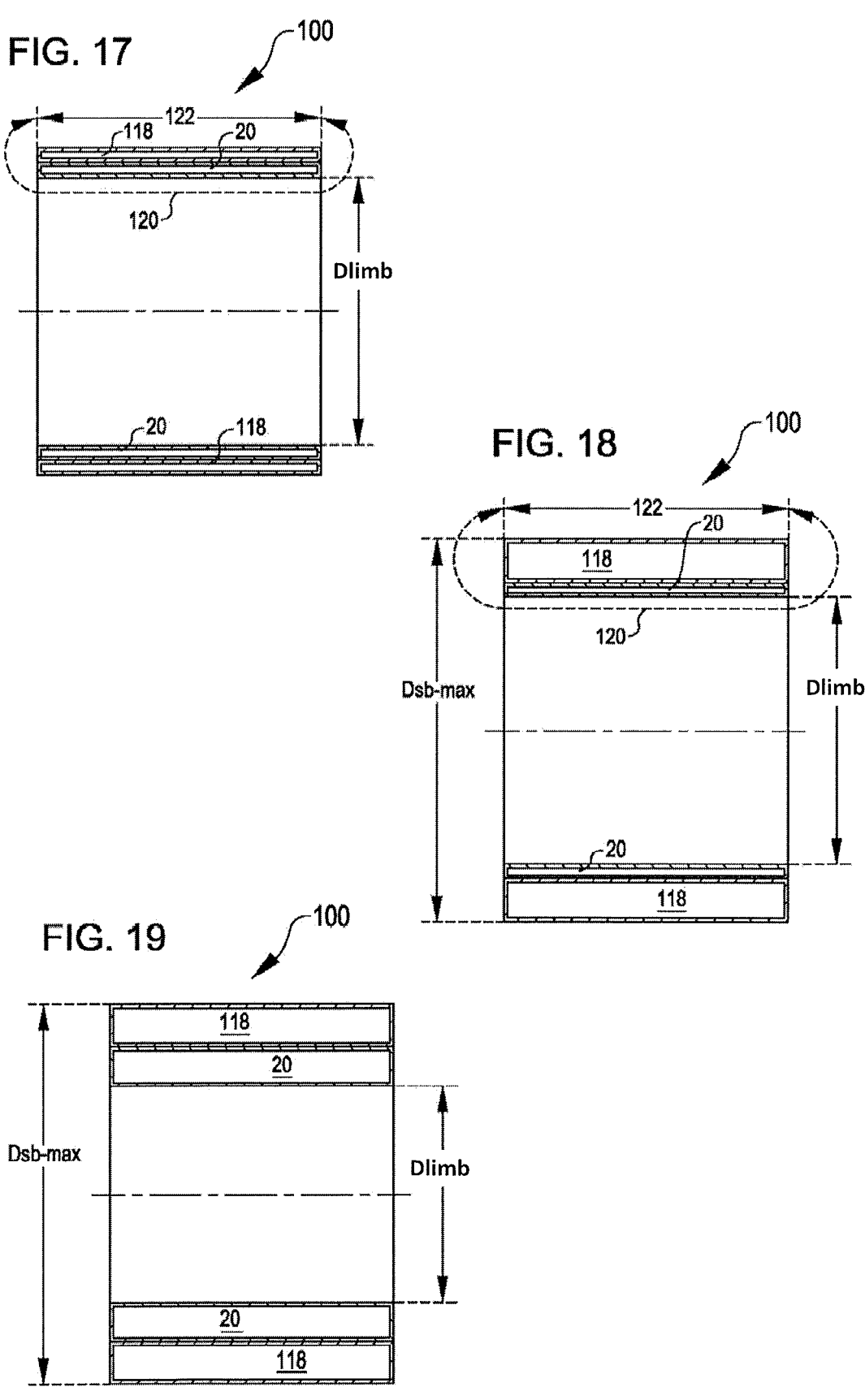

FIG. 17 is a cross-sectional view of an ambulatory blood pressure cuff that includes an inflatable support band and an inflatable bladder supported by the inflatable support band, in accordance with embodiments.

FIG. 18 is a cross-sectional view of the ambulatory blood pressure cuff of FIG. 17 with the inflatable support band inflated and the inflatable bladder deflated.

FIG. 19 is a cross-sectional view of the ambulatory blood pressure cuff of FIG. 17 with the inflatable support band inflated and the inflatable bladder inflated.

Figure 20:
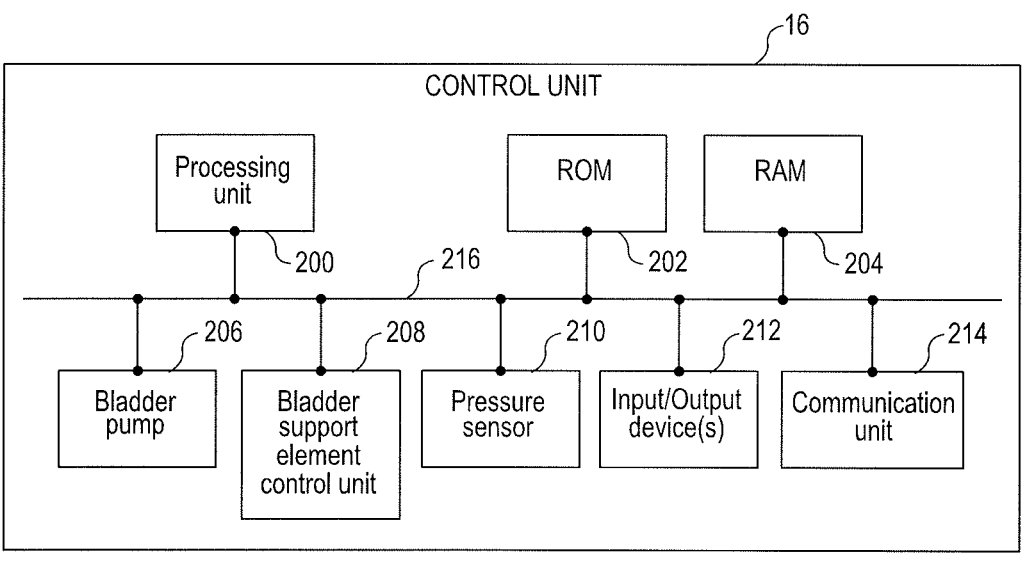

FIG. 20 is a simplified schematic diagram of a control unit of the blood pressure cuff of FIG. 1.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Turning now to the drawings in which like reference identifiers refer to like elements in the various figures, FIG. 1A shows an embodiment of an ambulatory blood pressure measurement device 10. In the embodiment illustrated in FIG. 1A, the blood pressure measurement device 10 is configured to be worn on a wrist of a user 12. The ambulatory blood pressure measurement device 10 includes a band assembly 14 and a control unit 16 mounted to the band assembly 14. The band assembly 14 includes a support band 18 and an inflatable bladder 20 mounted to the support band 18. The inflatable bladder 20 is inflated and deflated by the control unit 16 to measure a blood pressure of the user 12. As described in more detail herein, the support band 18 is reconfigurable, by the control unit 16, between a flexible standby configuration for between blood pressure measurements and a measurement configuration in which the support band 18 provides suitable support to the inflatable bladder 20 during inflation of the bladder 20 during measurement of a blood pressure of the user 12. In the flexible standby configuration, the support band 18 is configured to flex and circumferentially stretch so as to limit the pressure that the band assembly 14 applies to the wrist of the user 12 to a comfortable level throughout changes in circumferential size and/or shape of the wrist of the user 12 that can occur when the user 12 moves and/or flexes the user's wrist. Additionally, in the embodiments of the support band 14 described herein, the band assembly 14 can be configured for use with a range of different wrist sizes while still limiting the pressure that the band assembly 14 applies to the wrist of the user 12 to a comfortable level. In such embodiments, the support band 18 can have a circumferential in-plane stiffness that is suitably low enough to limit the pressure applied to the wrist of the user 12 for a suitable range of different circumferences of the wrist of the user 12.

In some embodiments, the wrist-worn ambulatory blood pressure measurement device 10 is configured with watch and/or smart-watch functionality. For example, the functionality of the control unit 16 can be incorporated and/or combined into any suitable wrist-worn device (e.g., watch, smart watch, wrist-worn fitness tracking device). In some embodiments, the support band 18 has a first end coupled to one side of the control unit 16 and a second end that coupleable to a second side of the control unit 16 to secure the device 10 to the wrist of the user 12. In some embodiments, the device 10 includes an adjustment mechanism operable to adjust the circumferential length of the device 10 suitable to accommodate any of a suitable range of wrist circumferences. For example, the second end of the support band 18 can include a suitable number of attachment features distributed circumferentially along a length of the support band 18 with each of the attachment features being configured for selective coupling to the second side of the control unit 16 for selective configuration of the circumferential length of the device 10 suitable for a particular wrist circumference.

In some embodiments, the wrist-worn blood pressure measurement device 10 is configured for use in conjunction with a smart watch or a fitness tracking device (e.g., a wrist-worn fitness tracking device). For example, FIG. 1B shows an embodiment of the wrist-worn blood pressure measurement device 10 configured to worn on a wrist of a user 12 for use in conjunction with a smart watch 11. In some embodiments, the control unit 16 includes a wireless communication unit that utilizes a suitable wireless communication protocol (e.g., Bluetooth, WiFi, and the like) to communicatively couple the wrist-worn blood pressure measurement device 10 with the smart watch 11. In some embodiments, operation of the device 10 is controlled by the smart watch 11 via wireless communication between the smart watch 11 and the device 10. While FIG. 1B shows the device 10 worn adjacent to the smart watch 11, any of the embodiments of the blood pressure measurement device 10 described herein can be configured for use in conjunction with a smart watch or a fitness tracking device. In some embodiments, the control unit 16 includes one or more input devices (e.g., an input button and/or a touch screen) configured to accept control input from the user 12 on which the control unit 16 bases control of the device 10.

The ambulatory blood pressure measurement device 10 can be configured to be worn on any suitable limb (and location of the limb) of a user 12. For example, FIG. 1C shows an embodiment of the ambulatory blood pressure measurement device 10 configured to be worn on a thigh of a user. As another example, FIG. 1D shows an embodiment of the ambulatory blood pressure measurement device 10 configured to be worn on an upper arm of a user.

FIG. 2 and FIG. 3 are cross-sectional views of the band assembly 14 in the flexible standby configuration. FIG. 2 shows the band assembly 14 at a first circumference 22, which can correspond to a limb circumference of a first user. FIG. 3 shows the band assembly 14 at a second circumference 24, which is substantially larger than the first circumference 22 and can correspond to a limb circumference of a second user having a larger limb than the first user. In many embodiments, the support band 18 band has a limited circumferential in-plane stiffness in the flexible standby configuration so as to facilitate flexibility over a range limb sizes. Since the support band 18 can be configured to accommodate different size limbs of different users while still limiting the pressure applied to the limb to a comfortable level while in the flexible standby configuration, the support band 18 can accommodate movement and/or flexing of a user's limb without applying pressure to the limb that exceeds a comfortable level while in the flexible standby configuration.

FIG. 4 shows the band assembly 14 in the measurement configuration in which the support band 18 has a circumference 26 and the inflatable bladder 20 is in an inflated state. In the measurement configuration, the support band 18 has an circumferential in-plane stiffness that is substantially increased relative to the circumferential in-plane stiffness in the flexible standby configuration. In many embodiments, the control unit 16 is operatively coupled with the support band 18 and selectively reconfigures the support band 18 between the flexible standby configuration and the measurement configuration.

Various alternate embodiments of the band assembly 14 are described herein that employ alternate embodiments of the support band 18. Common elements in the embodiments of the band assembly 14 described herein are identified using the same reference identifiers. Similar elements in the embodiments of the band assembly 14 described herein are identified with similar reference identifiers that employ the same first two numbers. For example, FIG. 5 is a cross-sectional view of an embodiment 14a of the band assembly 14 in which the support band 18a includes a reinforcement sheet 28a embedded within a highly stretchable band 30 (e.g., a stretchable fabric band). The stretchable band 30 can be configured to expand through a wide range of diameters to facilitate flexibility over a range of limb sizes. The reinforcement sheet 28a extends circumferentially around the support band 18a so as to overlap itself in an overlap sector 32a. The reinforcement sheet 28a can be made from a suitable thickness of a suitable material (e.g., a fabric mesh, polyamide or other high-modulus polymer) so as to have a circumferential in-plane stiffness that is substantially higher than the circumferential in-plane stiffness of the stretchable band 30. Within the overlap sector 32a, electrodes 34 with overlaying conformal dielectric layers 36 (e.g., silicone) are formed on interfacing portions of the reinforcement sheet 28a.

In the flexible standby configuration of the support band 18a, the same voltage is applied to each of the electrodes 34 thereby preventing electrostatic binding between the electrodes 34 so as to accommodate relative slippage between the conformal dielectric layers 36. Since the circumference of the reinforcement sheet 28a is free to change in the flexible standby configuration, the reinforcement sheet 28a does not contribute significantly to the circumferential stiffness of the support band 18a in the flexible standby configuration. As a result, the circumferential stiffness of the support band 18a in the flexible standby configuration is substantially provided by the stretchable band 30.

In the measurement configuration of the support band 18a, a different voltage is applied to each of the electrodes 34 thereby producing electrostatic binding between the conformal dielectric layers 36. Since slippage between the conformal dielectric layers 36 is prevented in the measurement configuration, the reinforcement sheet 28a contributes substantially to the circumferential stiffness of the support band 18a in the measurement configuration. As a result, the circumferential in-plane stiffness of the support band 18a in the measurement configuration is substantially increased relative to the circumferential in-plane stiffness of the support band 18a in the flexible standby configuration. In some embodiments, the different voltage is applied to the electrodes 34 shortly after starting to inflate the bladder 20 during a blood pressure measurement cycle. Following completion of the blood pressure measurement, the same voltage is applied to the electrodes 34 to reconfigure the support band 18a back to the flexible standby configuration from the measurement configuration.

FIG. 6 shows an embodiment 14b of the band assembly 14a in which the reinforcement sheet 28b includes separate circumferentially extending end portions 38b1, 38b2. The end portions 38b1 on one end of the reinforcement sheet 28b interleave with the end portions 38b2 on the other end of the reinforcement sheet 28b. In the illustrated embodiment, side surfaces of the end portions 38b1, 38b2 are coplanar to a respective plane perpendicular to a central axis 40 of the band assembly 14b, and engagement between side surfaces of the end portions 38b1 and side surfaces of the end portions 38b2 helps to maintain alignment of the reinforcement sheet 28b during expansion and contraction of the circumference of the reinforcement sheet 28b to accommodate the size of a user's limb and to accommodate movement and/or flexure of the user's limb. Each of the end portions 38b1, 38b2 overlap a respective region of the corresponding opposite end of the reinforcement sheet 28b. Within the respective overlapping regions, electrodes 34 with overlaying conformal dielectric layers 36 are formed on interfacing portions of the reinforcement sheet 28a. The electrodes 34 of the band assembly 14b are activated as with the band assembly 14a to reconfigured the band assembly 14b from the flexible standby configuration to the measurement configuration.

FIG. 7 is a cross-sectional view of a band assembly 14c for an embodiment of the ambulatory blood pressure cuff 10. The band assembly 14c includes a support band 18c that includes two overlapping reinforcement sheets 28c1, 28c2 with surface electrodes 34 that are energized to bind the reinforcement sheets 28c1, 28c2 together to form a continuous reinforcement band to reconfigure the band assembly 14c from the flexible standby configuration to the measurement configuration. In the illustrated embodiment, each of the reinforcement sheets 28c1, 28c2 is embedded within the stretchable band 30 and extends circumferentially around the support band 18c through a sector less than 360 degrees, thereby forming a gap between opposite ends of each of the reinforcement sheets 28c1, 28c2. The reinforcement sheets 28c1, 28c2 are oriented 180 degrees from each other, thereby ensuring that misalignment of the gaps. Surface electrodes 34 formed on the reinforcement sheets 28c1, 28c2 are energized to bind the reinforcement sheets 28c1, 28c2 together to form a continuous reinforcement band to reconfigure the blood pressure cuff from the flexible standby configuration to the measurement configuration.

FIG. 8 through FIG. 10 are cross-sectional views of a band assembly 14d for an embodiment of the ambulatory blood pressure cuff 10. The band assembly 14d includes a support band 18d that includes longitudinally extending sheet reinforcement sheets segments 28d1, 28d2. In the illustrated embodiment, each of the reinforcement sheets 28d1, 28d2 is embedded within the stretchable band 30 and extends longitudinally along the support band 18d. Each of the reinforcement sheets 28d1 have end portions, each of which overlaps a respective end portion of an adjacent one of the reinforcement sheets 28d2. Surface electrodes 34 formed on the reinforcement sheets 28d1, 28d2 are energized to bind the reinforcement sheets 28d1, 28d2 together to form a continuous reinforcement band to reconfigure the blood pressure cuff from the flexible standby configuration (illustrated in FIG. 9) to the measurement configuration (illustrated in FIG. 10).

FIG. 11 shows a band assembly 14e for an embodiment of the ambulatory blood pressure cuff 10. The band assembly 14e includes a support band 18e that includes circumferentially extending sheet reinforcement sheets segments 28e1, 28e2. In the illustrated embodiment, each of the reinforcement sheets 28e1, 28e2 is embedded within the stretchable band 30 and extends circumferentially around the support band 18e similar to the reinforcement sheets 28c1, 28c2 in the band assembly 14c. Each of the reinforcement sheets 28e1 overlap an adjacent one or two of the reinforcement sheets 28e2. Surface electrodes 34 formed on the reinforcement sheets 28e1, 28e2 are energized to bind the reinforcement sheets 28e1, 28e2 together to form one or more continuous reinforcement bands to reconfigure the blood pressure cuff from the flexible standby configuration to the measurement configuration.

FIG. 12 shows a band assembly 14f for an embodiment of the ambulatory blood pressure cuff 10. The band assembly 14f includes a support band 18f that includes two-dimensional patterns of reinforcement sheet segments 28/1, 28/2. In the illustrated embodiment, each of the reinforcement sheet segments 28/1, 28/2 is embedded within the stretchable band 30. Each of the reinforcement sheet segments 28/1 overlap an adjacent two or four of the reinforcement sheets 28/2. Surface electrodes 34 formed on the reinforcement sheet segments 28/1, 28/2 are energized to bind the reinforcement sheet segments 28/1, 28/2 together to form a continuous reinforcement band to reconfigure the blood pressure cuff from the flexible standby configuration to the measurement configuration.

FIG. 13 illustrates an electrostatic vent assembly 50 that can be employed in embodiments of the ambulatory blood pressure cuff 10. FIG. 14 is a side cross-sectional view of the electrostatic vent assembly 50. The electrostatic vent assembly 50 includes a vent cover 52 that can be mounted the inflatable bladder 20 to cover a vent hole 54, which can be formed in the inflatable bladder 20. In the illustrated embodiment, the vent assembly 50 includes a hinge 56 by which the vent cover 52 is pivotally mounted to the inflatable bladder 20. In alternate embodiments, an end portion of the vent cover 52 is attached to the bladder 20 and cross-sectional bending of the vent cover 52 adjacent to the end portion occurs during opening of the vent assembly 20. Similar to the embodiments of the support band 18 described herein, electrodes 34 and associated overlaying conformal dielectric layers 36 are formed on interfacing portions of the vent cover 52 and the bladder 50. Activation of the electrodes 34 electrostatically seals the vent cover 52 to the bladder 20, thereby sealing the vent hole 54. Application of the same voltage to each of the electrodes 34 results in lack of electrostatic attraction between the electrodes 34, thereby enabling pressurized air within the bladder 20 to open the vent cover 52 and escape through the vent hole 54. In the illustrated embodiment, the vent assembly 50 includes a tether 58 connected between the vent cover 52 and the bladder 20. The tether 58 can be configured to limit the opening of the vent cover 52 so that subsequent activation of the electrodes 34 is effective in closing the vent cover 52. In some embodiments, the vent assembly 50 includes a spring mechanism configured to return the vent cover 52 to the closed configuration following venting of the air from the bladder 20. The vent assembly 50 functions as a unidirectional valve that is operable to selectively vent air in one direction (e.g., toward the outside of the bladder 20 when the vent cover 52 is disposed on the outside of the bladder 20). To enable bi-directional venting, an additional vent assembly 50 can be employed with the vent cover 52 disposed inside the bladder 20.

FIG. 15 shows a band assembly 14g for an embodiment of the ambulatory blood pressure cuff 10. The band assembly 14g can employ any of the embodiments of the support band 18 described herein. The band assembly 14g includes an embodiment 20a of the inflatable bladder 20. The inflatable bladder 20a includes one or more side chambers that can be selectively inflated/deflated to vary the longitudinal width of the bladder 20a (for example, from W1 to W2 and vice versa) to better accommodate the length of a particular user's limb. For example, FIG. 16 shows an embodiment of the inflatable bladder 20a that includes a selectively inflatable side chamber 20a-side, inflation electrostatic vent assemblies 50i, and deflation electrostatic vent assemblies 50d. The inflation electrostatic vent assemblies 50i and the deflation electrostatic vent assemblies 50d are configured the same as the electrostatic vent assembly 50 described herein. The electrodes 34 of the inflation electrostatic vent assemblies 50i can be supplied the same voltage to open the vent assemblies 50i to inlet air into the side chamber 20a-side from the main chamber of the bladder 20a. The electrodes 34 of the deflation electrostatic vent assemblies 50d can be supplied a suitable voltage differential to seal the vent assemblies 50d closed to prevent escape of air from the side chamber 20a-side. To deflate the side chamber 20a-side, the electrodes 34 of the deflation electrostatic vent assemblies 50d can be supplied the same voltage to open the vent assemblies 50d to vent air from the side chamber 20a-side to the surrounding environment and/or to the main chamber of the bladder 20a.

FIG. 17 through FIG. 19 are cross-sectional views of an ambulatory blood pressure cuff 100 that includes an inflatable support band 118 and an inflatable bladder 20 supported by the inflatable support band 118, in accordance with embodiments. FIG. 17 shows the blood pressure cuff 100 with each of the bladder 20 and the support band 118 deflated. When in the deflated state, the support band 118 is configured to expand through a wide range of diameters (D-limb) to facilitate flexibility over a range of limb sizes. For example, the inflatable support band 118 can include an inner membrane portion 120 and an outer membrane portion 122. The inner membrane portion 120 can be configured with a circumferential in-plane stiffness similar to the stretchable band 30 described herein. The outer membrane portion 122 can have an outer circumference sized to accommodate the expansion of the inflatable support band 118 up to a maximum outer diameter Dsb-max (shown in FIG. 18). The outer membrane portion 122 can have a circumferential in-plane stiffness sufficient to react internal pressure within the support band 118 without significant diametrical expansion of the outer membrane portion 122 beyond the maximum outer diameter Dsb-max. For example, both the inner membrane portion 120 and the outer membrane portion 122 can include reinforcing fibers that extend perpendicular to the circumferential direction of the support band 118 so as to not contribute significantly to the circumferential in-plane stiffness of either of the inner membrane portion 120 and the outer membrane portion 122. The outer membrane portion 122 can further include additional reinforcing fibers that extend in the circumferential direction of the support band so as to substantially increase the circumferential in-plane stiffness of the outer membrane portion 122 over the circumferential in-plane stiffness of the inner membrane portion 120.

In embodiments, the inflatable support band 118 and the inflatable bladder 20 are kept at the same internal pressure levels via simultaneous inflation/deflation, thereby ensuring that the outer membrane portion 122 provides full support to the inflatable bladder 20 during an inflation/deflation cycle used to measure a blood pressure of the user. When the support band 118 is in the deflated state, the outer membrane portion 122 is configured to have a collapsed configuration in which the outer membrane portion 122 has local circumferential curvature variations if the outer diameter of the outer membrane portion 122 is less than the maximum outer diameter Dsb-max. FIG. 19 is a cross-sectional view of the ambulatory blood pressure cuff 100 with the inflatable support band 118 inflated and the inflatable bladder 20 inflated during measurement of a blood pressure of the user 12.

FIG. 20 is a simplified schematic diagram of the control unit 16 of the blood pressure cuff 10. The control unit 16 is configured to control operation of the band assembly 14 to accomplish measurements of the blood pressure of the user 12. The control unit 16 includes a processing unit 200, read-only memory (ROM) 202, random-access memory (RAM) 204, a bladder pump 206, a bladder support element control unit 208, a pressure sensor 210, one or more input/ output devices 212, a communication unit 214, and a communication bus 216. Each of the ROM 202, RAM 204, the bladder pump 206, the bladder support element control unit 208, the pressure sensor 210, the input/output device(s) 212, and the communication unit 214 is communicatively coupled with the processing unit 200 via the communication bus 216.

The ROM 202 and/or the RAM 204 can store instructions executable by the processor 200. For example, the ROM 202 can store operating system instructions executable by the processing unit 200. The RAM 204 can store program instructions executable by the processor 200 for controlling operation of the band assembly 14 to accomplish measurements of the blood pressure of the user 12. Measured blood pressure values can be stored in the RAM 204 and/or output via the input/output device(s) 212 and/or via the communication unit 214. In some embodiments, the communication unit 214 includes a suitable wireless communication unit operable to transmit the measured blood pressure values to a suitable user device. In some embodiments, the input/ output device(s) 212 include a suitable output port via which measured blood pressure values stored in the RAM 204 can be transmitted to a suitable user device for subsequent evaluation. A schedule for blood pressure measurements can be input into the control unit 16 via the input/output device (s) 212 and/or via the communication unit 214. The processing unit 200 can include a clock for use in determining when to accomplish scheduled blood pressure measurements.

To accomplish a blood pressure measurement, the processing unit 200 can control operation of the bladder pump 206 to accomplish a suitable inflation/deflation cycle of the inflatable bladder 20 over which the blood pressure is measured. The bladder pump 206 is operatively connected with the inflatable bladder 20 via a suitable pressurized air conduit. In some embodiments, following a short amount of time following the start of the inflation/deflation cycle of the inflatable bladder, the processing unit 200 controls the bladder support element control unit 208 to energize the electrodes 34 of the support band 18 to reconfigure the support band 18 from the flexible standby configuration to the measurement configuration. The bladder support element control unit 208 is electrically connected to the electrodes 34 and operable to apply a suitable voltage differential (e.g., 100 to 200 volts) to the electrodes 34 to generate electrostatic binding between the conformal dielectric surfaces 36 as described herein. In alternate embodiments in which the band assembly employs an inflatable support band 118, the inflatable support band 118 can be inflated/deflated via the bladder pump 206 at the same rate and pressure as described herein. During the inflation/deflation cycle, the processing unit 200 monitors the pressure in the inflatable bladder 20 via an output signal generated by the pressure sensor 210. The pressure sensor 210 is operatively connected to the inflatable bladder 20 via a suitable conduit. Using known techniques, the processing unit 200 detects the systolic blood pressure and the diastolic blood pressure during the deflation portion of the inflation/deflation cycle. Following completion of the blood pressure measurement, the processing unit 200 controls the bladder support element control unit 208 to de-energize the electrodes 34 of the support band 18 to reconfigure the support band 18 from the measurement configuration back to the flexible standby configuration.

The devices and approaches described herein may be used in support of collecting blood pressure data and/or may be used in conjunction with collection of personal data that relates to the user's health, personal data that enables identification of the user, and/or personal data that can be used to contact and/or locate the user, or any specific person. For example, the personal data can include data regarding a user's state of health of fitness, such as physiological data, medication information, exercise data). The personal data can include date of birth, home address, email address, telephone number(s), location data, and/or demographic data.

The user's personal data, including physiological data such as blood pressure data generated via the use of the devices and approaches described herein, can be used to benefit the user. For example, the blood pressure data may facilitate monitoring of the user's blood pressure and/or other aspects of the user's health and/or physical fitness.

It is expected that entities engaged in collection, analysis, disclosure, transfer, storage, or other use of such personal data will comply with applicable privacy requirements, policies, and/or practices. For example, it is expected that such entities will implement and comply with privacy policies and privacy practices that are generally recognized as meeting or exceeding applicable requirements (e.g., governmental laws and regulation, industry standards) for ensuring privacy and security of personal information. The privacy policies and practices should be easily accessible by users. The privacy policies and practices should be updated in response to changes in the collection and/or use of the personal data. Personal data of users should be collected for legitimate and reasonable uses by the entity. Personal data of users should not be sold and/or shared outside of the legitimate and reasonable uses of the entity. Additionally, collection and sharing of personal data should require informed consent of the user. Entities should consider taking additional steps to safeguard and secure access to the personal data and to ensure that others with access to the personal data comply with the applicable privacy procedures and privacy practices. Additionally, entities can implement evaluation by a third party to ensure compliance by the entity with the applicable privacy practices and privacy policies. The applicable privacy practices and privacy policies may vary or otherwise be adapted for the applicable geographic region and/or the specific nature and type of the personal data.

Even though entities should protect personal data of a user as described above, embodiments of the devices and approaches described herein can be configured for users to selectively block the collection of, use of, or access to, personal data, including physiological data such as blood pressure data. In some embodiments, a user may be able to disable hardware and/or software elements that collect physiological data. Additionally, some embodiments can include hardware and/or software elements operable to prevent or block access to personal data previously collected. For example, in some embodiments, a user many be able to remove, disable, and/or restrict collection of the user's personal data.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

Examples of the embodiments of the present disclosure can be described in view of the following clauses:

Clause 1. A blood pressure cuff comprising: an inflatable bladder; a support band attached to and surrounding the inflatable bladder, the support band being reconfigurable, in response to an input, from a standby configuration for between blood pressure measurements to a measurement configuration for constraining the inflatable bladder while the inflatable bladder is in an inflated state during a blood pressure measurement, a circumferential stiffness of the support band being at least 50 percent greater in the measurement configuration than in the standby configuration; and a control unit comprising a bladder pump for inflation of the inflatable bladder during a blood pressure measurement and a support band control unit for supplying the input to the support band.

Clause 2. The blood pressure cuff of clause 1, wherein the circumferential stiffness of the support band is at least 100 percent greater in the measurement configuration than in the standby configuration.

Clause 3. The blood pressure cuff of clause 1, wherein the circumferential stiffness of the support band is at least 200 percent greater in the measurement configuration than in the standby configuration.

Clause 4. The blood pressure cuff of any one of clauses 1 through 3, wherein: the support band comprises a sheet of a material extending circumferentially around the support band over greater than 360 degrees; a first surface electrode is formed on a first end portion of the sheet; a second surface electrode is formed on a second end portion of the sheet separated from the first end portion by an intervening portion of the sheet; the first surface electrode and the second surface electrode overlap; the first surface electrode and the second surface electrode are operatively connected to the support band control unit for activation via the input; separation between the first surface electrode and the second surface electrode accommodates slippage between the first surface electrode and the second surface electrode when the first surface electrode and the second surface electrode are not activated via the input; and activation of the first surface electrode and the second surface electrode via the input electrostatically binds the first surface electrode and the second surface electrode so as to prevent slippage between the first surface electrode and the second surface electrode.

Clause 5. The blood pressure cuff of clause 4, wherein at least one of the first end portion and the second end portion comprises at least two isolated circumferentially extending portions.

Clause 6. The blood pressure cuff of clause 4, wherein the sheet is embedded within a stretchable fabric band.

Clause 7. The blood pressure cuff of any one of clauses 1 through 3, wherein: the support band comprises a first sheet of a material extending circumferentially around the support band and a second sheet of a material extending circumferentially around the support band; a first surface electrode is formed on the first sheet; a second surface electrode is formed on the second sheet; the first surface electrode and the second surface electrode overlap; the first surface electrode and the second surface electrode are operatively connected to the support band control unit for activation via the input; separation between the first surface electrode and the second surface electrode accommodates slippage between the first surface electrode and the second surface electrode when the first surface electrode and the second surface electrode are not activated via the input; and activation of the first surface electrode and the second surface electrode via the input electrostatically binds the first surface electrode and the second surface electrode so that the first sheet and the second sheet are connected to form a continuous reinforcement ring in the measurement configuration.

Clause 8. The blood pressure cuff of clause 7, wherein the first sheet and the second sheet are embedded within a stretchable fabric band.

Clause 9. The blood pressure cuff of any one of clauses 1 through 3, wherein: the support band comprises a first plurality of longitudinally extending sheet segments and a second plurality of longitudinally extending sheet elements; first surface electrodes are formed on the first plurality of longitudinally extending sheet segments; second surface electrodes are formed on the second plurality of longitudinally extending sheet segments; each of the first surface electrodes overlaps each of an adjacent pair of the second surface electrodes; the first surface electrodes and the second surface electrodes are operatively connected to the support band control unit for activation via the input; separation between the first surface electrodes and the second surface electrodes accommodates slippage between the first surface electrodes and the second surface electrodes when the first surface electrodes and the second surface electrodes are not activated via the input; and activation of the first surface electrodes and the second surface electrodes via the input electrostatically binds the first plurality of longitudinally extending sheet segments and the second plurality of longitudinally extending sheet elements to form a continuous reinforcement ring in the measurement configuration.

Clause 10. The blood pressure cuff of clause 9, wherein the first plurality of longitudinally extending sheet segments and the second plurality of longitudinally extending sheet elements are embedded within a stretchable fabric band.

Clause 11. The blood pressure cuff of any one of clauses 1 through 3, wherein: the support band comprises a first plurality of circumferentially extending sheet segments and a second plurality of circumferentially extending sheet elements; first surface electrodes are formed on the first plurality of circumferentially extending sheet segments; second surface electrodes are formed on the second plurality of circumferentially extending sheet segments; each of the first surface electrodes overlaps at least one of the second surface electrodes; the first surface electrodes and the second surface electrodes are operatively connected to the support band control unit for activation via the input; separation between the first surface electrodes and the second surface electrodes accommodates slippage between the first surface electrodes and the second surface electrodes when the first surface electrodes and the second surface electrodes are not activated via the input; and activation of the first surface electrodes and the second surface electrodes via the input electrostatically binds the first plurality of circumferentially extending sheet segments and the second plurality of circumferentially extending sheet elements to form one or more continuous reinforcement rings in the measurement configuration.

Clause 12. The blood pressure cuff of clause 11, wherein the first plurality of circumferentially extending sheet segments and the second plurality of circumferentially extending sheet elements are embedded within a stretchable fabric band.

Clause 13. The blood pressure cuff of any one of clauses 1 through 3, wherein: the support band comprises a first plurality of sheet segments arranged in a first two-dimensional pattern and a second plurality of sheet elements arranged in a second two-dimensional pattern; first surface electrodes are formed on the first plurality of sheet segments; second surface electrodes are formed on the second plurality of sheet segments; each of the first surface electrodes overlaps at least two of the second surface electrodes; the first surface electrodes and the second surface electrodes are operatively connected to the support band control unit for activation via the input; separation between the first surface electrodes and the second surface electrodes accommodates slippage between the first surface electrodes and the second surface electrodes when the first surface electrodes and the second surface electrodes are not activated via the input; and activation of the first surface electrodes and the second surface electrodes via the input electrostatically binds the first plurality of sheet segments and the second plurality of sheet elements to form one or more continuous reinforcement rings in the measurement configuration.

Clause 14. The blood pressure cuff of clause 13, wherein the first plurality of sheet segments and the second plurality of sheet elements are embedded within a stretchable fabric band.

Clause 15. The blood pressure cuff of any one of clauses 1 through 3, wherein the bladder comprises an electrostatically sealable vent operable to vent air from the bladder, the electrostatically sealable vent comprising a vent cover coupled with the bladder and configured to seal a vent hole in the bladder, a vent cover electrode being formed on the vent cover, a vent hole electrode formed on the bladder and surrounding the vent hole, the vent cover electrode and the vent hole electrode being operatively connected to the control unit.

Clause 16. The blood pressure cuff of any one of clauses 1 through 3, wherein the electrostatically sealable vent comprises a tether connected to the vent cover and configured to limit an open orientation of the vent cover.

Clause 17. The blood pressure cuff of any one of clauses 1 through 3, wherein: the bladder comprises an expansion chamber that is inflatable to increase a longitudinal length of the bladder; and the bladder comprises a plurality of electrostatically sealable vents operatively connected to the support band control unit and operable to inflate and deflate the expansion chamber.

Clause 18. A blood pressure cuff comprising: an inflatable bladder; an inflatable support band attached to and surrounding the inflatable bladder, the inflatable support band having an uninflated configuration for between blood pressure measurements and an inflated configuration for constraining the inflatable bladder while the inflatable bladder is in an inflated state during a blood pressure measurement; and a control unit comprising at least one pump for inflating the inflatable support band and the inflatable bladder for a blood pressure measurement.

Clause 19. The blood pressure cuff of clause 18, wherein: the inflatable support band comprises an outer wall, an inner wall, and side walls that connect the outer wall to the inner wall; the inner wall has an inner wall circumferential in-plane stiffness; and the outer wall has an outer wall circumferential in-plane stiffness that is at least 100 percent greater than the inner wall circumferential in-plane stiffness.

Clause 20. A method for measuring a blood pressure of a person, the method comprising: supporting an inflatable bladder in an uninflated state via a support band attached to and surrounding the inflatable bladder so as to maintain contact between the inflatable bladder in the uninflated state and a limb of the person; supplying, via a control unit operatively coupled with the support band, an input to the support band that reconfigures the support band from a standby configuration having a standby configuration circumferential stiffness to a measurement configuration having a measurement configuration circumferential stiffness that is at least 50 percent greater than the standby configuration circumferential stiffness; and with the support band in the measurement configuration, measuring, by the control unit, a blood pressure of the patient via an inflation of the inflatable bladder.

Clause 21. The method of clause 20, further comprising, subsequent to the measurement of the blood pressure, reconfiguring the support band, via the control unit, from the measurement configuration to the standby configuration.

Clause 22. The method of any one of clauses 20 and 21, wherein supplying the input to the support band comprises supplying a voltage to electrodes formed on one or more reinforcement sheets so as to electrostatically bind the electrodes.

Clause 23. A method for measuring a blood pressure of a person, the method comprising: supporting an inflatable bladder in an uninflated state via an inflatable support band attached to and surrounding the inflatable bladder so as to maintain contact between the inflatable bladder in the uninflated state and a limb of the person; inflating the inflatable support band, via a control unit operatively coupled with the inflatable support band; and, with the support band inflated, measuring, by the control unit, a blood pressure of the patient via an inflation of the inflatable bladder.

Clause 24. The method of clause 23, further comprising, subsequent to the measurement of the blood pressure, deflating the support band via the control unit.

What is claimed is:

1. A blood pressure cuff comprising:
an inflatable bladder;
a support band attached to and encircling the inflatable bladder, wherein the support band is reconfigurable, in response to an input, from a standby configuration for between blood pressure measurements to a measurement configuration for constraining the inflatable bladder during an inflation of the inflatable bladder during a blood pressure measurement, wherein the support band comprises one or more reinforcement sheets, and wherein the input comprises a voltage applied to electrodes formed on the one or more reinforcement sheets so as to electrostatically bind the electrodes; and
a control unit comprising a bladder pump for the inflation of the inflatable bladder during the blood pressure measurement and a support band control unit for supplying the input to the support band.

2. The blood pressure cuff of claim 1, wherein:
the one or more reinforcement sheets comprises a first sheet of a material extending circumferentially around the support band over greater than 360 degrees;

a first surface electrode is formed on a first end portion of the first sheet;

a second surface electrode is formed on a second end portion of the first sheet separated from the first end portion by an intervening portion of the first sheet;

the first surface electrode and the second surface electrode overlap;

the first surface electrode and the second surface electrode are operatively connected to the support band control unit for activation via the input;

separation between the first surface electrode and the second surface electrode accommodates slippage between the first surface electrode and the second surface electrode when the first surface electrode and the second surface electrode are not activated via the input; and activation of the first surface electrode and the second surface electrode via the input electrostatically binds the first surface electrode and the second surface electrode so as to prevent slippage between the first surface electrode and the second surface electrode.

3. The blood pressure cuff of claim 2, wherein at least one of the first end portion and the second end portion comprises at least two isolated circumferentially extending portions.

4. The blood pressure cuff of claim 2, wherein the first sheet is embedded within a stretchable fabric band.

5. The blood pressure cuff of claim 1, wherein:

the one or more reinforcement sheets comprises a first sheet of a material extending circumferentially around the support band and a second sheet of a material extending circumferentially around the support band;

a first surface electrode is formed on the first sheet;

a second surface electrode is formed on the second sheet;

the first surface electrode and the second surface electrode overlap;

the first surface electrode and the second surface electrode are operatively connected to the support band control unit for activation via the input;

separation between the first surface electrode and the second surface electrode accommodates slippage between the first surface electrode and the second surface electrode when the first surface electrode and the second surface electrode are not activated via the input; and activation of the first surface electrode and the second surface electrode via the input electrostatically binds the first surface electrode and the second surface electrode so that the first sheet and the second sheet are connected to form a continuous reinforcement ring in the measurement configuration.

6. The blood pressure cuff of claim 5, wherein the first sheet and the second sheet are embedded within a stretchable fabric band.

7. The blood pressure cuff of claim 1, wherein:

the one or more reinforcement sheets comprises a first plurality of longitudinally extending sheet segments and a second plurality of longitudinally extending sheet segments;

first surface electrodes are formed on the first plurality of longitudinally extending sheet segments;

second surface electrodes are formed on the second plurality of longitudinally extending sheet segments;

each of the first surface electrodes overlaps each of an adjacent pair of the second surface electrodes;

the first surface electrodes and the second surface electrodes are operatively connected to the support band control unit for activation via the input;

separation between the first surface electrodes and the second surface electrodes accommodates slippage between the first surface electrodes and the second surface electrodes when the first surface electrodes and the second surface electrodes are not activated via the input; and activation of the first surface electrodes and the second surface electrodes via the input electrostatically binds the first plurality of longitudinally extending sheet segments and the second plurality of longitudinally extending sheet segments to form a continuous reinforcement ring in the measurement configuration.

8. The blood pressure cuff of claim 7, wherein the first plurality of longitudinally extending sheet segments and the second plurality of longitudinally extending sheet segments are embedded within a stretchable fabric band.

9. The blood pressure cuff of claim 1, wherein:

the one or more reinforcement sheets comprises a first plurality of circumferentially extending sheet segments and a second plurality of circumferentially extending sheet segments;

first surface electrodes are formed on the first plurality of circumferentially extending sheet segments;

second surface electrodes are formed on the second plurality of circumferentially extending sheet segments;

each of the first surface electrodes overlaps at least one of the second surface electrodes;

the first surface electrodes and the second surface electrodes are operatively connected to the support band control unit for activation via the input;

separation between the first surface electrodes and the second surface electrodes accommodates slippage between the first surface electrodes and the second surface electrodes when the first surface electrodes and the second surface electrodes are not activated via the input; and activation of the first surface electrodes and the second surface electrodes via the input electrostatically binds the first plurality of circumferentially extending sheet segments and the second plurality of circumferentially extending sheet segments to form one or more continuous reinforcement rings in the measurement configuration.

10. The blood pressure cuff of claim 9, wherein the first plurality of circumferentially extending sheet segments and the second plurality of circumferentially extending sheet segments are embedded within a stretchable fabric band.

11. The blood pressure cuff of claim 1, wherein:

the one or more reinforcement sheets comprises a first plurality of sheet segments arranged in a first two-dimensional pattern and a second plurality of sheet segments arranged in a second two-dimensional pattern;

first surface electrodes are formed on the first plurality of sheet segments;

second surface electrodes are formed on the second plurality of sheet segments;

each of the first surface electrodes overlaps at least two of the second surface electrodes;

the first surface electrodes and the second surface electrodes are operatively connected to the support band control unit for activation via the input;

separation between the first surface electrodes and the second surface electrodes accommodates slippage between the first surface electrodes and the second surface electrodes when the first surface electrodes and the second surface electrodes are not activated via the input; and activation of the first surface electrodes and the second surface electrodes via the input electrostatically binds the first plurality of sheet segments and the second plurality of sheet segments to form one or more continuous reinforcement rings in the measurement configuration.

12. The blood pressure cuff of claim 11, wherein the first plurality of sheet segments and the second plurality of sheet segments are embedded within a stretchable fabric band.

13. The blood pressure cuff of claim 1, wherein the inflatable bladder comprises an electrostatically sealable vent operable to vent air from the inflatable bladder, the electrostatically sealable vent comprising a vent cover coupled with the inflatable bladder and configured to seal a vent hole in the inflatable bladder, a vent cover electrode being formed on the vent cover, a vent hole electrode formed on the inflatable bladder and surrounding the vent hole, the vent cover electrode and the vent hole electrode being operatively connected to the control unit.

14. The blood pressure cuff of claim 13, wherein the electrostatically sealable vent comprises a tether connected to the vent cover and configured to limit an open orientation of the vent cover.

15. The blood pressure cuff of claim 1, wherein:

the inflatable bladder comprises an expansion chamber that is inflatable to increase a longitudinal length of the inflatable bladder; and the inflatable bladder comprises a plurality of electrostatically sealable vents operatively connected to the support band control unit and operable to inflate and deflate the expansion chamber.

16. A method for measuring a blood pressure of a person, the method comprising:

supporting an inflatable bladder in an uninflated state via a support band attached to and encircling the inflatable bladder so as to maintain contact between the inflatable bladder in the uninflated state and a limb of the person, wherein the support band comprises one or more reinforcement sheets;

supplying, via a control unit operatively coupled with the support band, an input to the support band that reconfigures the support band from a standby configuration to a measurement configuration, wherein supplying the input to the support band comprises supplying a voltage to electrodes formed on the one or more reinforcement sheets so as to electrostatically bind the electrodes; and with the support band in the measurement configuration, measuring, by the control unit, a blood pressure of the person via an inflation of the inflatable bladder.

17. The method of claim 16, further comprising, subsequent to the measurement of the blood pressure, reconfiguring the support band, via the control unit, from the measurement configuration to the standby configuration.

* * * * *